US008063365B1

(12) United States Patent
Standiford et al.

(10) Patent No.: US 8,063,365 B1
(45) Date of Patent: Nov. 22, 2011

(54) NON-SHOT-NOISE-LIMITED SOURCE FOR ELECTRON BEAM LITHOGRAPHY OR INSPECTION

(75) Inventors: Keith Standiford, Carmel, CA (US); Alan Brodie, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 273 days.

(21) Appl. No.: 12/326,518

(22) Filed: Dec. 2, 2008

(51) Int. Cl.
*G01N 23/00* (2006.01)
(52) U.S. Cl. ......... 250/310; 250/306; 250/307; 250/311
(58) Field of Classification Search .................. 250/306, 250/307, 310, 311, 492.1, 492.2, 492.3
See application file for complete search history.

(56) References Cited

U.S. PATENT DOCUMENTS

| | | | |
|---|---|---|---|
| 6,596,999 B2 * | 7/2003 | Golladay et al. ........... 250/423 F |
| 6,870,172 B1 * | 3/2005 | Mankos et al. ........... 250/492.22 |
| 6,878,937 B1 | 4/2005 | Mankos et al. |
| 6,943,360 B1 * | 9/2005 | Mankos ...................... 250/492.2 |
| 2001/0008274 A1 * | 7/2001 | Nakasuji ...................... 250/492.3 |
| 2002/0148975 A1 * | 10/2002 | Kimba et al. .............. 250/492.1 |
| 2003/0085364 A1 * | 5/2003 | Golladay et al. ........... 250/492.2 |
| 2003/0111619 A1 * | 6/2003 | Ito ............................ 250/492.23 |
| 2004/0159787 A1 * | 8/2004 | Nakasuji et al. .............. 250/311 |
| 2005/0121611 A1 * | 6/2005 | Kimba et al. ................. 250/311 |
| 2008/0308729 A1 * | 12/2008 | Kimba et al. ................. 250/307 |
| 2009/0057558 A1 * | 3/2009 | Iwaya et al. .................. 250/311 |

* cited by examiner

*Primary Examiner* — Michael Maskell
(74) *Attorney, Agent, or Firm* — Okamoto & Benedicto LLP

(57) ABSTRACT

One embodiment relates to an electron source apparatus for an electron beam lithography tool or an electron beam inspection tool. A cathode is configured to emit electrons, and an anode is configured to accelerate the electrons so as to create an electron beam. There are no beam apertures in the electron source apparatus that are positioned at non-focal planes. An electron lens may be configured to focus the electron beam to form a cathode image at a focal plane, and a beam aperture may positioned at the focal plane. Other embodiments, aspects and features are also disclosed.

11 Claims, 3 Drawing Sheets

100

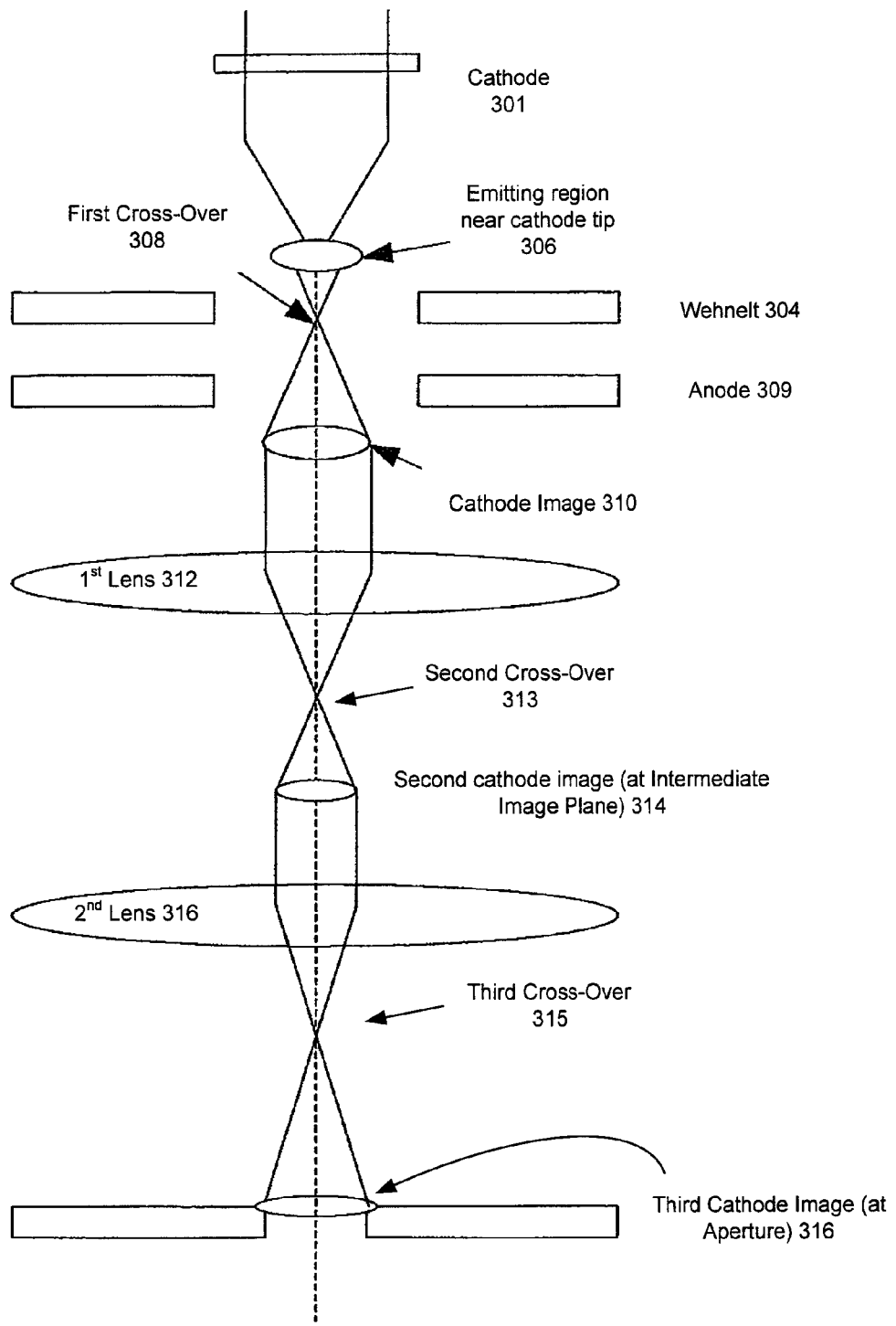
FIG. 3    102 or 210

NON-SHOT-NOISE-LIMITED SOURCE FOR ELECTRON BEAM LITHOGRAPHY OR INSPECTION

STATEMENT REGARDING FEDERALLY SPONSORED RESEARCH OR DEVELOPMENT

This invention was made with Government support under Agreement No. HR0011-07-9-0007 awarded by DARPA. The Government has certain rights in the invention.

BACKGROUND

1. Technical Field

The present invention relates generally to semiconductor manufacturing and related technologies. More particularly, the present invention relates to electron beam apparatus for use in lithography or inspection tools.

2. Description of the Background Art

The present disclosure provides a novel and inventive electron source which has use in either electron beam lithography or automated electron beam inspection (or review) systems.

As is known in the art, electron beam lithography systems may be categorized as electron beam direct write (EBDW) or electron beam projection systems. In EBDW lithography, the substrate is sequentially exposed by means of a focused electron beam, wherein the beam either scans in the form of lines over the whole specimen and the desired structure is written on the object by corresponding blanking of the beam, or, as in a vector scan method, the focused electron beam is guided over the regions to be exposed. The beam spot may be shaped by a diaphragm. In electron beam projection lithography, analogously to optical lithography, a larger portion of a mask is illuminated simultaneously and is imaged on a reduced scale on a wafer by means of projection optics. Since a whole field is imaged simultaneously in electron beam projection lithography, the attainable throughputs can be markedly higher in comparison with electron beam writers.

As is also known, automated electron beam inspection (or review) systems may be classified as either scanning or projection systems. Scanning electron beam systems are more commonplace and operate by scanning an electron beam across a region of a substrate surface to obtain image data. On the other hand, projection electron beam systems operate by simultaneously projecting a wider electron beam over a larger area and by using a position-sensitive detection system to detect data for an array of pixels in parallel.

BRIEF DESCRIPTION OF THE DRAWINGS

FIG. 3 is a schematic diagram of an electron source which is configured so as to be non-shot-noise limited in accordance with an embodiment of the invention.

SUMMARY

One embodiment relates to an electron source apparatus for an electron beam lithography tool or an electron beam inspection tool. A cathode is configured to emit electrons, and an anode is configured to accelerate the electrons so as to create an electron beam. There are no beam apertures in the electron source apparatus that are positioned at non-focal planes. An electron lens may be configured to focus the electron beam to form a cathode image at a focal plane, and a beam aperture may positioned at the focal plane.

Another embodiment relates to an apparatus for electron beam lithography. The apparatus includes at least an electron source, an electron reflective patterned structure, a stage and a beam separator. The electron source includes a cathode configured to emit electrons and an anode configured to accelerate the electrons so as to create an electron beam. There are no beam apertures in the electron source that are positioned at non-focal planes. The electron reflective patterned structure is configured to have at least two voltage levels applied thereto. The stage is configured to hold a target substrate. The beam separator is configured to bend a trajectory of the electron beam from the electron source towards the electron reflective patterned structure and to bend the trajectory of the electron beam from the electron reflective patterned structure towards the stage.

Another embodiment relates to an apparatus for automated electron beam inspection of substrates. The apparatus includes at least an electron source, a stage, an electron detection system, and a beam separator. The electron source includes a cathode configured to emit electrons and an anode configured to accelerate the electrons so as to create an electron beam. There are no beam apertures in the electron source that are positioned at non-focal planes. The stage is configured to hold a substrate to be inspected. The beam separator is configured to bend a trajectory of the electron beam from the electron source towards the stage and to bend the trajectory of the electron beam from the stage towards the electron detection system.

Another embodiment relates to a method of generating an electron beam for use in lithography or inspection. Electrons are emitted from a cathode, and the electrons are accelerated so as to create an electron beam. The electron beam is focused to form a cathode image at a focal plane, and a beam aperture is provided at the focal plane. There are no beam apertures which are provided at non-focal planes, and the electron beam has a signal-to-noise ratio below a shot noise limit.

Other embodiments, aspects and feature are also disclosed.

DETAILED DESCRIPTION

Maskless Reflection Electron Beam Lithography

Figure 1:
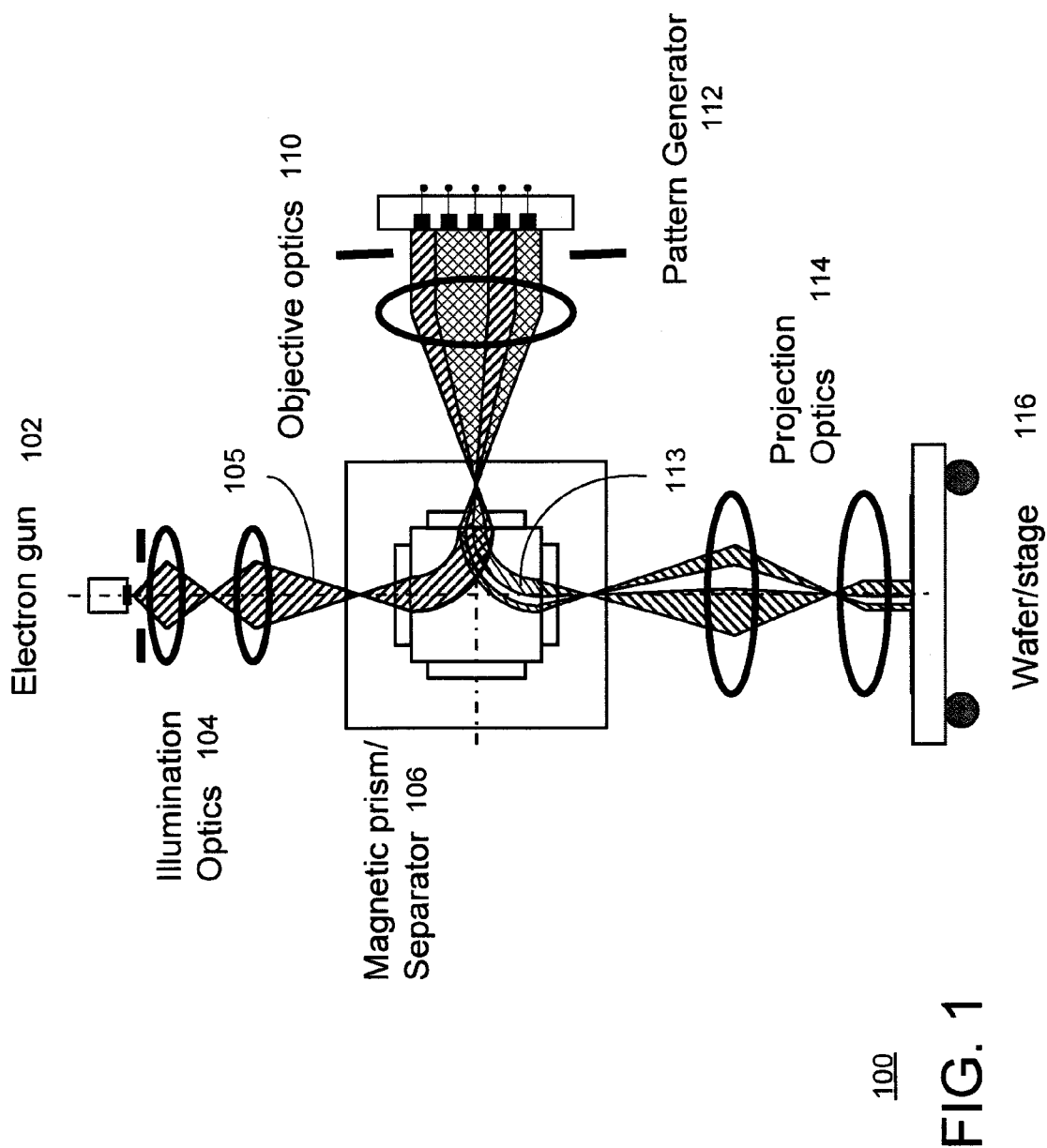
FIG. 1 is a schematic diagram of a maskless reflection electron beam projection lithography column which may incorporate a non-shot-noise limited source in accordance with an embodiment of the invention.

FIG. 1 is a schematic diagram of a single maskless reflection electron beam projection lithography column 100 in accordance with an embodiment of the invention. The name may be abbreviated to a reflection electron beam lithography or REBL system. As depicted, the column 100 includes an electron source 102, illumination electron-optics 104, a magnetic prism 106, objective electron optics 110, a dynamic pattern generator (DPG) 112, projection electron-optics 114, and a stage 116 for holding a wafer or other target to be lithographically patterned. In accordance with an embodiment of the invention, the various components of the column 100 may be implemented as follows.

The electron source 102 may be implemented so as to have a low energy spread. This is because the REBL system 100 should preferably control the energy of the electrons so that their turning points (the distance above the DPG 112 at which they reflect) are relatively constant, for example, to within about a hundred nanometers. In accordance with an embodiment of the invention, the electron source 102 is configured to be a non-shot-limited source, as described further below in relation to FIG. 3.

The illumination electron-optics 104 is configured to receive and collimate the electron beam from the source 102. The illumination optics 104 allows the setting of the current illuminating the pattern generator structure 112 and therefore determines the electron dose used to expose the substrate. The illumination optics 104 may comprise an arrangement of magnetic and/or electrostatic lenses configured to focus the electrons from the source 102 so as to generate an incident electron beam 105. The specific details of the arrangement of lenses depend on specific parameters of the apparatus and may be determined by one of skill in the pertinent art.

The magnetic prism 106 is configured to receive the incident beam 105 from the illumination optics 104. When the incident beam traverses the magnetic fields of the prism, a force proportional to the magnetic field strength acts on the electrons in a direction perpendicular to their trajectory (i.e. perpendicular to their velocity vectors). In particular, the trajectory of the incident beam 105 is bent towards the objective optics 110 and the dynamic pattern generator 112. In one embodiment, the magnetic prism 106 is configured with a non-uniform magnetic field so as to provide stigmatic focusing, for example, as disclosed in U.S. Pat. No. 6,878,937, issued Apr. 12, 2005 to Marian Mankos, entitled "Prism Array for Electron Beam Inspection and Defect Review," and assigned at issuance to KLA-Tencor Technologies Corporation of Milipitas, Calif. The disclosure of the aforementioned in U.S. Pat. No. 6,878,937 is hereby incorporated by reference. A uniform magnetic field provides astigmatic focusing wherein focusing occurs in only one direction (for example, so as to image a point as a line). In contrast, the magnetic prism 106 configuration should focus in both directions (so as to image a point as a point) because the prism 106 is also utilized for imaging. The stigmatic focusing of the prism 106 may be implemented by dividing it into smaller sub-regions with different but uniform magnetic fields. Furthermore, the lens elements in the prism 106 may be of a relatively longer length and width so as to provide for a low distortion image over a large field size. However, increasing the length of the prism 106 involves a trade-off of more electron-electron interactions causing more blur. Hence, the reduced image distortion should be balanced against the increased blur when increasing the prism length.

Below the magnetic prism 106, the electron-optical components of the objective optics are common to the illumination and projection subsystems. The objective optics 110 may be configured to include an objective lens and one or more transfer lenses. The objective optics 110 receives the incident beam from the prism 106 and decelerates and focuses the incident electrons as they approach the DPG 112. The objective optics is preferably configured (in cooperation with the gun 102, illumination optics 104, and prism 106) as an immersion cathode lens and is utilized to deliver an effectively uniform current density (i.e. a relatively homogeneous flood beam) over a large area in a plane above the surface of the DPG 112. The dynamic pattern generator 112 comprises an array of pixels. Each pixel may comprise a metal contact to which a voltage level is controllably applied.

The extraction part of the objective optics 110 provides an extraction field in front of the DPG 112. As the reflected electrons 113 leave the DPG 112, the objective optics is configured to accelerate the reflected electrons 113 toward their second pass through the prism 106. The prism 106 is configured to receive the reflected electrons 113 from the transfer lens 108 and to bend the trajectories of the reflected electrons towards the projection optics 114.

The projection electron-optics 114 reside between the prism 106 and the wafer stage 116. The projection optics 114 is configured to focus the electron beam and demagnify the beam onto photoresist on a wafer or onto another target. The wafer stage 116 holds the target wafer.

E-Beam Inspection Apparatus

Figure 2:
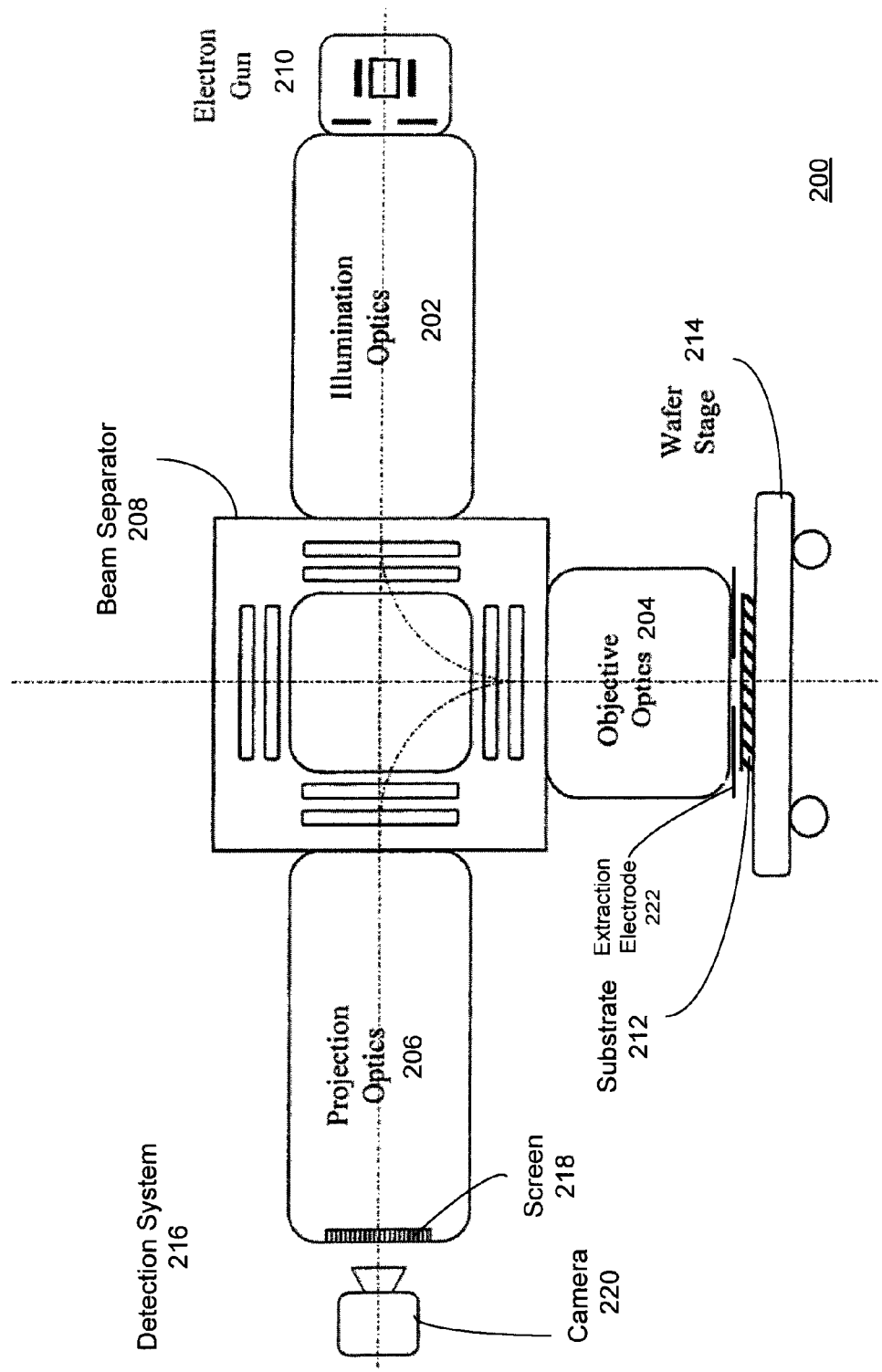
FIG. 2 is a schematic diagram of an automated electron beam inspection apparatus which may incorporate a non-shot-noise limited source in accordance with an embodiment of the invention.

FIG. 2 is a schematic diagram depicting an apparatus 200 for inspecting a substrate using an electron beam in accordance with an embodiment of the invention. The apparatus 200 includes an illumination subsystem 202, an objective subsystem 204, a projection subsystem 206, and a beam separator 208. The beam separator 208 is coupled to and interconnects the illumination subsystem 202, the objective subsystem 204, and the projection subsystem 206.

The illumination subsystem (illumination optics) 202 is configured to receive and collimate electrons from an electron source or gun 210. In accordance with an embodiment of the invention, the electron gun 210 is configured to be a non-shot-limited source, as described further below in relation to FIG. 3.

The beam separator 208 is configured to receive the incident beam from the illumination subsystem 202 and to bend or deflect the incident beam by 90 degrees into the objective subsystem 204. In one embodiment, the beam separator 208 comprises a magnetic prism array including a central magnetic section, an inner magnetic section outside the central section, and an outer magnetic section outside the inner section. Such a magnetic prism array is described in further detail, for example, in the aforementioned U.S. Pat. No. 6,878,937 to Mankos.

The objective subsystem (objective optics) 204 is configured to receive the incident beam from the beam separator 208 and to decelerate and focus the incident beam onto the substrate 212. The incident beam onto the substrate 208 causes reflection and/or emission of a scattered beam of charged particles. The scattered beam comprises a two-dimensional image of the illuminated area of the substrate 212. The objective optics 204 is further configured to re-accelerate the scattered beam and to refocus the two-dimensional image of the substrate area. The objective optics 204 includes an extraction electrode 222.

The beam separator 208 is configured to receive the scattered beam from the objective optics 204 and to bend the scattered beam towards the projection subsystem 206. The projection subsystem (projection optics) 206 is configured to receive the scattered beam from the beam separator 208 and to magnify and project the scattered beam onto a detector 216. In this way, a magnified two-dimensional image of the illuminated substrate area is obtained. In one embodiment, the detector 216 may comprise a phosphorescent screen 218 and a camera 220 as depicted. In another embodiment, the detector 216 may include a charge-coupled device (CCD) array.

Conventional Sources for E-Beam Lithography or Inspection

Applicants note that previous electron sources for e-beam lithography or inspection may be categorized into sources that are space-charge limited and sources that are not space-charge limited. These conventional sources (whether space-charge limited or not) generally perform with noise content at or above the shot-noise limit. Shot noise occurs when the emission of a finite number of particles (such as electrons) gives rise to statistical fluctuations.

Previous electron sources which are not space-charge limited generally have noise content at or above the shot-noise limit. These sources include thermal sources and field emission sources.

Previous electron sources which are space-charge limited, when used in lithographic or inspection applications, tend to perform at the shot-noise limit. Applicants note that these sources are usually utilized in a manner which rejects part of the electron beam. The rejection of current is generally accomplished by limiting the angle of emission from the cathode, or by imaging a crossover onto a shaping aperture. Limiting the beam current in these ways randomizes the electron distribution because the angular distribution is random, resulting in the performance being shot-noise limited.

Hence, in the above-described previous sources, beam noise cannot be reduced much below the shot-noise limit. This limit effectively bounds the lower detection limits and throughputs of inspection tools and the lithographic quality and throughput of lithography tools. The beam noise sets the lower limit of the system because other components typically add noise.

Data-Rate Requirement and Signal-to-Noise Limitation

One practical challenge for e-beam lithography or inspection is the achievement of a high data rate. For example, data rates on the order of tens of terabits per second may be required in order to use electron beam lithography in semiconductor manufacturing. Such a high data rate is needed to perform e-beam lithography with sufficiently high throughput to be economically viable. Similarly, a high data rate is also needed to perform e-beam inspection at a high throughput rate.

The throughput of e-beam lithography or inspection is fundamentally limited by the signal-to-noise ratio (SNR) of the electron beam used. Applicants note, as discussed above, that the noise content of an electron beam is usually limited by shot noise (which, in theory, is due to the detected electrons having a Poisson distribution). It is an objective of the present disclosure to provide an electron source that delivers a beam which delivers a high SNR by lowering the noise content below the shot noise limit and the associated Poisson distribution.

Non-Shot-Noise Limited Electron Source

The present application discloses an electron source for lithography or inspection which has noise performance which is substantially better than the shot-noise limit. In other words, the disclosed source design circumvents the shot-noise limit.

In regard to improving performance beyond the shot-noise limit, applicants note that electrons become correlated by the space-charge cloud in front of the cathode. The source design disclosed herein avoids destroying this correlation characteristic. For example, the design avoids selection of electrons based on emission angle. This is because selection based on emission angle introduces a randomness that destroys some of the aforementioned correlation.

In accordance with an embodiment of the invention, the electron source is configured to image the emission region (which is some small distance away from the cathode surface) directly onto the substrate area to be exposed or inspected, depending on the application. For electron beam lithography, this means imaging the emission region onto the dynamic pattern generator. For electron beam inspection, this means imaging the emission region onto the semiconductor wafer being inspected.

The design disclosed herein does not limit the angular extent of the beam using conventional beam limiting apertures. This is because, at planes where the source is not in focus, partitioning the beam removes portions of the beam based on emission angle, which introduces randomness. Rather, if the area covered by the beam is to be limited, then an aperture is used at a focal plane to prevent destruction of the space-charge cloud correlation. This works because the electron beam is spatially correlated at focal planes.

FIG. 3 is a schematic diagram of an electron source (102 or 210) which is configured so as to be non-shot-noise limited in accordance with an embodiment of the invention. The cathode 301 for the electron source is shown towards the top of the figure. A Wehnelt electrode (cap) 304 may be configured as a convergent electrostatic lens to converge the emitted electrons into an electron cloud at the emitting region 306.

The electrons are accelerated from the emitting region 306 towards the anode 309 of the source. In accordance with an embodiment of the invention, the Wehnelt electrode 304 and the anode 309 together act as an electron lens which forms a first cross-over 308 between the emitting region 306 and the anode 309. Furthermore, the Wehnelt 304 and the anode 309 cause the electron beam to form a cathode image 310 which is an image of the electron cloud of the emitting region 306.

In further accordance with an embodiment of the invention, a first electron lens 312 is configured such that the electron beam forms a second cross-over 313 and a second cathode image 314, the second cathode image 314 being formed at an intermediate image plane. In addition, a second electron lens 314 is configured such that the electron beam forms a third cross-over 315 and a third cathode image 316, the third cathode image 316 being formed at an aperture.

Applicants have determined that it is advantageous to aperture the beam, if at all, only at a focal plane of the beam. In other words, any beam aperture should be at a plane in which a virtual image of the electron cloud of the emitting region 306 is formed (i.e any beam aperture should be positioned at a focal plane, and no beam aperture should be positioned at a non-focal plane). In the particular embodiment described above, the only aperture is positioned at the same plane as the third cathode image 316. Such a configuration is advantageous because it avoids the consequence of destroying the electron correlation of the space-charge cloud.

This approach avoids using any conventional beam-limiting aperture which is not located at a focal plane. Such conventional beam-limiting apertures limit the angular extent of the beam and in doing so generally partition the beam based on emission angle. Applicants believe that this partitioning of the beam based on emission angle introduces randomness into the electron distribution which destroys electron correlation of the space-charge cloud and so causes the electron source to be shot-noise limited. By avoiding destruction of the electron correlation, applicants have invented an apparatus for an electron source which is non-shot noise limited.

Inspection and lithography generally require a minimum signal-to-noise ratio (SNR) to meet specified performance requirements. If the noise limit is Poissonian (i.e. shot noise), this minimum SNR sets a minimum number of electrons that must be used to inspect or expose each pixel. As the patterns of interest continue to shrink, this minimum number of electrons per pixel causes the total number of electrons needed to increase with the inverse square of the feature sizes.

Such inspection and lithographic tools are typically designed for the maximum possible current which gives the resolution required. Increasing the current is difficult, since electron interactions decrease resolution as current is increased. Indeed, improvements in resolution are generally also required as the feature sizes shrink, forcing the current to decrease as well.

The current available and the total number of electrons required for the lithography or the inspection determines the throughput of the tool. By providing an electron source which has a noise-limit lower than the shot-noise limit in accordance with an embodiment of the invention, the tool throughput will generally increase in direct proportion to this improvement.

In accordance with an embodiment of the invention, the electron source is space-charge limited. Substantially all electrons from the source are utilized by the system, unless the electrons are removed at a plane where the source is in focus (i.e. a focal plane). The source may be a point source or a source with a large area. Large-area sources may be imaged onto samples being inspected or onto pattern generators (such as dynamic pattern generators discussed above, shaping apertures or arrays of apertures), Intermediate image planes and beam crossovers may be configured in the illumination system, or not (i.e. they are optional).

CONCLUSION

Advantageously, by using the apparatus and methods disclosed above in accordance with embodiments of the invention, the throughput for an electron lithography or inspection apparatus may be greatly increased.

The above-described diagrams are not necessarily to scale and are intended be illustrative and not limiting to a particular implementation. In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron gun for an electron beam lithography tool or an electron beam inspection tool, the electron gun comprising:
    a cathode configured to emit electrons;
    a Wehnelt electrode to form an electron cloud at an emitting region near the cathode;
    an anode configured to accelerate the electrons so as to create an electron beam,
    wherein the Wehnelt electrode and the anode together act to form a first cross-over between the emitting region and the anode within the electron gun and to form a first cathode image within the electron gun;
    a first electron lens configured to focus the electron beam to form a second cross-over within the electron gun and a second cathode image at an intermediate image plane within the electron gun;
    a beam aperture positioned at an exit of the electron gun;
    a second electron lens configured to focus the electron beam to form a third cross-over within the electron gun and a third cathode image at the beam aperture,
    wherein there are no beam apertures in the electron gun that are positioned at non-focal planes.

2. The electron gun of claim 1, wherein a signal-to-noise ratio of the electron beam is below a shot noise limit.

3. An apparatus for electron beam lithography, the apparatus comprising:
    an electron gun including
        a cathode configured to emit electrons,
        a Wehnelt electrode to form an electron cloud at an emitting region near the cathode,
        an anode configured to accelerate the electrons so as to create an electron beam,
        wherein the Wehnelt electrode and the anode together act to form a first cross-over between the emitting region and the anode within the electron gun and to form a first cathode image within the electron gun,
        a first electron lens configured to focus the electron beam to form a second cross-over within the electron gun and a second cathode image at an intermediate image plane within the electron gun,
        a beam aperture positioned at an exit of the electron gun,
        a second electron lens configured to focus the electron beam to form a third cross-over within the electron gun and a third cathode image at the beam aperture;
    illumination optics configured to receive and collimate electrons from the electron gun;
    an electron reflective patterned structure having at least two voltage levels applied thereto; and
    a stage to hold a target substrate; and
    a beam separator configured to bend a trajectory of the electron beam from the illumination optics towards the electron reflective patterned structure and to bend the trajectory of the electron beam from the electron reflective patterned structure towards the stage.

4. The apparatus of claim 3, wherein a signal-to-noise ratio of the electron beam is below a shot noise limit.

5. An apparatus for automated electron beam inspection of substrates, the apparatus comprising:
    an electron gun including
        a cathode configured to emit electrons,
        a Wehnelt electrode to form an electron cloud at an emitting region near the cathode,
        an anode configured to accelerate the electrons so as to create an electron beam,
        wherein the Wehnelt electrode and the anode together act to form a first cross-over between the emitting region and the anode within the electron gun and to form a first cathode image within the electron gun,
        a first electron lens configured to focus the electron beam to form a second cross-over within the electron gun and a second cathode image at an intermediate image plane within the electron gun,
        a beam aperture positioned at an exit of the electron gun,
        a second electron lens configured to focus the electron beam to form a third cross-over within the electron gun and a third cathode image at the beam aperture;
    illumination optics configured to receive and collimate electrons from the electron gun;
    a stage to hold a substrate to be inspected;
    an electron detection system; and
    a beam separator configured to bend a trajectory of the electron beam from the illumination optics towards the stage and to bend the trajectory of the electron beam from the stage towards the electron detection system.

6. The apparatus of claim 5, wherein a signal-to-noise ratio of the electron beam is below a shot noise limit.

7. A method of generating an electron beam for use in lithography or inspection, the method comprising:
   emitting electrons from a cathode,
   accelerating the electrons so as to create an electron beam;
   focusing the electron beam to form a cathode image at a focal plane; and
   providing a beam aperture at the focal plane,
   wherein there are no beam apertures which are provided at non-focal planes, and further wherein the electron beam has a signal-to-noise ratio below a shot noise limit wherein a Wehnelt electrode forms an electron cloud at an emitting region near the cathode, the Wehnelt electrode and an anode act together to form a first cross-over between the emitting region and the anode within the electron gun and to form a first cathode image within the electron gun, a first electron lens focuses the electron beam to form a second cross-over within the electron gun and a second cathode image at an intermediate image plane within the electron gun, and a second electron lens focuses the electron beam to form a third cross-over within the electron gun and a third cathode image at the beam aperture.

8. The method of claim 7, wherein the method is performed within an electron gun.

9. The method of claim 8, further comprising:
   forming a first cross-over and a first cathode image within the electron gun.

10. The method of claim 9, further comprising:
    forming a second cross-over and a second cathode image within the electron gun.

11. The method of claim 9, further comprising:
    forming a third cross-over within the electron gun.

* * * * *